US005487890A

United States Patent [19]
Taylor et al.

[11] Patent Number: 5,487,890
[45] Date of Patent: * Jan. 30, 1996

[54] MAMMALIAN PRIMATE ERYTHROCYTE BOUND HETEROPOLYMERIZED MONOCLONAL ANTIBODIES AND METHODS OF USE THEREOF

[75] Inventors: Ronald P. Taylor, Charlottesville; William M. Sutherland, Earlysville; Craig Reist, Charlottesville; Eleanor L. Wright, Earlysville; Donna Webb, Charlottesville; Ronald Labuguen, Charlottesville, all of Va.

[73] Assignee: University of Virginia Patent Foundation, Charlottesville, Va.

[*] Notice: The portion of the term of this patent subsequent to Nov. 28, 2012, has been disclaimed.

[21] Appl. No.: 186,136

[22] Filed: Jan. 24, 1994

Related U.S. Application Data

[63] Continuation of Ser. No. 161,812, Dec. 6, 1993, which is a continuation of Ser. No. 592,801, Oct. 4, 1990, abandoned.

[51] Int. Cl.$^6$ .................. A61K 39/395; A61K 39/40; A61K 39/42
[52] U.S. Cl. .................. 424/136.1; 424/142.1; 424/147.1; 424/150.1; 424/153.1; 435/70.21; 435/172.2; 435/240.27; 530/387.3; 530/388.15; 530/388.3; 530/388.4
[58] Field of Search .................. 424/136.1, 148.1, 424/160.1, 93.21, 93.73, 142.1, 147.1, 150.1, 153.1; 435/69.6, 69.7, 70.21, 172.2, 172.3, 240.2, 240.27; 530/387.3, 388.25, 388.35, 389.3, 389.4, 388.15, 388.3, 388.4

[56] References Cited

U.S. PATENT DOCUMENTS 4,433,059  2/1984  Chang et al. .................. 436/512

OTHER PUBLICATIONS

Edberg et al., "Quantitative Andyes Of The Binding Of Soluble Complement Fixing Antibody/dsDNA Immune Complexes To CR1 On Human Blood Cells" *J. Immunol.* 139(11):3739–3747, Dec. 1, 1987.

Titus et al., "Human K/Natural Killer Cells Targeted With Hetero–Cross–Linker Antibodies Specifically Lyse Tumor Cells In Vitro And Prevent Tumor Growth In Vivo," *J. Immunol.* 139(9):3153–3158, Nov. 1, 1987.

Karporsky et al, "Production Of Target Specific Effector Cells Using Hetero–Cross–Linked Aggregates Containing Anti-Target Cell and Anti–Fc$_\lambda$Receptor Antibodies," *J. Exp. Med.* 160:1686–1701, Dec., 1984.

Taylor et al., "In Vivo Binding And Clearance Of Circulating Antigen By Bispecific Heteropolymer–Medical Binding To Primate Erythrocyte Complement Receptor," *J. Immunol.* 148(8):2462–2468, Apr. 15, 1992.

Kimberly et al., "In Vivo Handling Of Soluble Complement Fixing Ab/dsDNA Immune Complexes In Chimpanzees," *J. Clin. Invest.* 84:962–970, Sep. 1989.

Reist et al., "Antigens Pre-Bound To The Primate Erythrocyte Complement Receptor Via Cross–linked Bispecific Monoclonal Antibody Heteropolymers Are Rapidly Cleared From The Circulatory," *Eur. J. Immunol.* 23:3021–3027, 1993.

*Primary Examiner*—Robert D. Budens
*Attorney, Agent, or Firm*—Oblon, Spivak, McClelland, Maier & Neustadt

[57] ABSTRACT

Mammalian red blood cells are used to safely and rapidly neutralize and/or clear antigens or immunogens from the circulatory system by binding to the RBC a monoclonal antibody specific for a receptor (CR1) on the RBC, which monoclonal antibody is chemically bound to a second Mab specific for the antigen to be cleared from the circulatory system. These chemically cross-linked monoclonal antibody heteropolymers may be injected directly into the patient's circulatory system. Alternatively, red blood cells, extracted from the patient or provided by a suitable donor, are bound to the Mab complex and returned to the system.

6 Claims, 2 Drawing Sheets

MAMMALIAN PRIMATE ERYTHROCYTE BOUND HETEROPOLYMERIZED MONOCLONAL ANTIBODIES AND METHODS OF USE THEREOF

This is a Continuation of application Ser. No. 08/161,812 filed on Dec. 6, 1993, which is a continuation of Ser. No. 07/592,801, filed on Oct. 4, 1990, now abandoned. This application is a continuation application of U.S. Ser. No. 08/161,812, pending, which is in turn a continuation of application of U.S. Ser. No. 07/592,801, abandoned.

BACKGROUND OF THE INVENTION

Field of the Invention

This invention is directed to mammalian primate erythrocytes to which have been bound cross-linked monoclonal antibodies (heteropolymers) specific for both the erythrocyte complement receptor protein (CR1), and (a 2nd antibody bound thereto specific for) a circulating antigen. Methods of using these "franked" erythrocytes in diagnostic or assay methodology and therapeutic applications are also addressed.

BACKGROUND OF THE PRIOR ART

Mammalian primate erythrocytes (RBC's) have been identified as essential to the body's ability to clear antibody/antigen immune complexes from the blood. Specifically, the RBC receptor (CR1), known to be specific for certain activated complement proteins (C3b, C3bi and C4b), has been implicated as playing an important role in the primate's defense against microorganism infection by facilitating the neutralization and clearance of certain pathogenic substances. Other evidence shows that the binding of these immune complexes to RBC's at the CR1 site provides a vehicle for rapid clearance of potentially pathogenic immune complexes from circulation. Enhancement of phagocytosis and circulatory-transport of immune complexes have both been advanced as mechanisms by which the RBC's function in this immune response. See, e.g., Nelson, *Science* 118, 733–737 (1953) and Hebert et al, *Kidney Int.*, 31, 877– 885 (1987). In any event, defects in aspects of this RBC clearance method have been demonstrated to be at least statistically related to a number of diseases and are believed to presage various disease activities.

Notwithstanding the importance of this function of the RBC and the immune system, it is apparent that the RBC binding and clearance capacity therefore is confined to immune complexes recognized by the CR1 receptor, that is the the immune complexes must contain large amounts of at least one of the activated Complement proteins C3b, C3bi, or C4b. Thus, the mammalian primate or human body has no normal capacity to take advantage of the clearance system provided by the RBC binding ability to remove antigens not complexed with the identified activated complement proteins. It remains an object of those of skill in the art to augment the natural capacity of the mammalian circulatory system to clear antigens through RBC binding ability to include the ability to bind immune complexes (antigen/antibody complexes) via CR1 to RBC's in the absence of activated complement proteins. These augmented RBC's would be useful both in a therapeutic sense, as well as in an assay mode to identify the presence or absence of specific antigens.

SUMMARY OF THE INVENTION

Specific monoclonal antibody heteropolymers are prepared from Mabs specific to the CR1 RBC receptor and Mabs to at least one other antigen and are then heteropolymerized using established techniques. This heteropolymer binds readily to RBC's in whole blood, in numbers in good agreement with the number of CR1 sites available. The RBC's, if franked in vivo with the heteropolymer, will then bind the antigen for which the remaining Mab is specific. These RBC's then can act therapeutically by facilitating the neutralization and clearance from the circulation of the bound antigen.

Alternatively, if introduced into a blood sample, franked RBC's bind quite rapidly to the antigen for which the second Mab is specific, and can also be used to assay for the presence of that particular antigen. If necessary, labeling of the heteropolymer and/or the antigen with, e.g., radioactive iodine, can facilitate bound RBC counts, and both qualitative and quantitative assessment of the antigen presence. Specificaly, the heteropolymer-franked RBC's can be used in clinical assays for antigens in the circulation as demonstrated by the following example: Franked RBC's would be added to the plasma or anti-coagulated blood and allowed to bind the putative target antigen. After a wash the presence of the antigen bound to the RBC's would be revealed using appropriately labelled (e.g. either with $^{125}$I, or enzyme-linked) second antibodies to the target antigen. Such assays can be either qualitative or quantitative.

RBC's removed and isolated may also be used as therapeutic agents. Once franked with heteropolymer, these RBC's can be reintroduced into the patient, where, in the bloodstream, free antigen will be bound and immobilized on the RBC, and cleared in accordance with the body's RBC clearing mechanism, which has been identified but is not completely understood. The franked RBC's can be specific for known antigens, such as HIV (the AIDS virus), or for substances which, if present in large amounts, can induce or aggravate disease states, such as low-density lipoproteins, or cause adverse biological effects, such as elevated hormone levels. Given the general ease with which Mabs can be prepared for any known antigen, the variety of franked RBC's imaginable is unlimited. Any antigen or immunogen found in the bloodstream can be addressed by this therapeutic method.

In an alternative embodiment, RBCs are franked with a "cocktail" of several heteropolymers which, in addition to binding the target antigen, also bind to several distinct and non-overlapping sites on CR1 of the RBC. These points are identified, by e.g., Mabs 1B4, HB8592, and 57F. Monoclonal antibody HB 8592 is commercially available from the American Type Culture Collection, Rockville, Md., U.S.A., 20852, registration ATCC HB 8592. Experiments have demonstrated that by using two or more non-overlapping Mabs for binding to CR1 on the RBC, the number of Mab heteropolymers that can be bound to a single RBC is increased in numbers in good agreement with the number of available binding sites. This augments the capability of a relatively small number of RBC's to bind to a relatively larger amount of antigen, and can further facilitate removal of the antigen through the normal immune clearance system.

BRIEF DESCRIPTION OF THE DRAWINGS

FIG. 1a reflects results with blood from a first donor, and illustrates the principle of additivity of binding sites. FIG. 1b reflects reduction in binding in blood lacking CR1 binding sites (Sheep blood).

DETAILED DESCRIPTION OF THE INVENTION

Figure 1A:
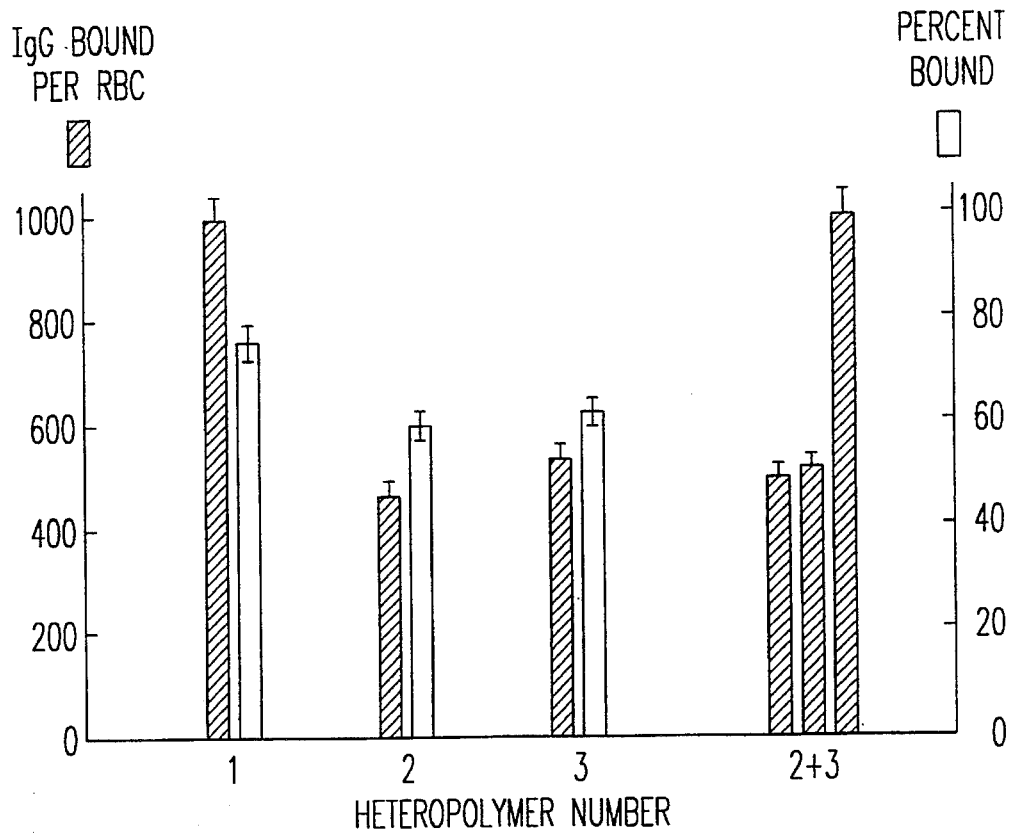
FIGS. 1a and 1b are column graphs reflecting binding of IgG per erythrocyte.

As noted above, the flexibility of the franked RBC's of this invention in addressing a variety of disease states is limited only by the varieties of different antigens present in or accessible to the circulatory system and to which Mab can be prepared. A variety of Mab heteropolymers have been prepared. In order to attach to the RBC, the antigen-specific Mab is cross-linked with a Mab to the RBC complement receptor, CR1. Methods of cross-linking these antibodies are known to those of skill in the art. In the examples set forth below, cross-linked heteropolymers were prepared using N-succinimidyl 3-(2-pyridyldithio)propionate (SPDP) according to established, published procedures. For details as to this procedure, see, e.g., Karpovsky et al, *J. Exp. Med.* 160, 1686–1701 (1984); Perez et al, *Nature,* 316, 354–356 (1985) or Titus et al, *Journal of Immunology,* 139, 3153–3158 (1987). Other procedures are known to those of ordinary skill in the art. A full listing of Mab heteropolymers prepared appears in Table 1, infra. Prototype antigens selected for targeting through preparation of appropriate heteropolymers include dinitrophenylated bovine gamma globulin ($DNP_{55}BGG$), and human IgG. Both antigens and heteropolymers were iodinated by the IODOGEN method (Fraker et al, *Biochem. Biophys. Res. Commun.* 80, 849–857 (1978). Iodination provides one protocol for assay utilization, but of course need not be practiced for the therapeutic aspects of the claimed invention.

Assays for CR1 levels on isolated RBC's followed standard methods, revealing about 200–500 epitopes per RBC, as bound to by anti-CR1 Mabs 1B4, 3D9 and HB8592.

Details regarding RBC binding, binding kinetics and observed values follow below.

EXAMPLES

1) Direct sensitization and binding isotherm analyses: Between 0.1 and 1.0 ml of a 10%–50% dispersion of washed RBC's in bovine serum albumin/phosphate buffered saline (BSA-PBS) were reacted for 1 hr at room temperature, with shaking, with varying amounts (10–50 ul) of a dilution of one or more of the heteropolymers. The RBC's were then washed 3 times in BSA-PBS (to remove excess unbound heteropolymer) and, after reconstitution in either BSA-PBS or normal human serum (for experiments with $^{125}$I-human IgG and $DNP_{55}BGG$, respectively), mixed with a small volume of $^{125}$I-probe. After a further incubation (usually 1 hr at room temperature, with shaking), RBC-bound and free $^{125}$I-antigens were separated by either of two procedures: RBC's were spun through oil (typically 150 ul of reaction mixture was layered on 200 ul of a dibutyl-dinonyl phthalate mixture), or simply processed by two cycles of centrifugation and washing in BSA-PBS. RBC-associated $^{125}$I counts were quantitated in a Beckman 5500 gamma counter.

2) "Whole Blood" binding kinetics: a) In most procedures blood was drawn into Alsever's and centrifuged. A portion of the supernatant was removed, and after the blood cells were redispersed to a final hematocrit of 50%, a small amount of $^{125}$I-$DNP_{55}BGG$ antigen was added. Varying amounts of heteropolymer were added directly to aliquots of these "whole blood" dispersions containing $^{125}$I-$DNP_{55}$ BGG, and incubated with shaking at 37° C. RBC associated $^{125}$I counts were determined at varying time points after centrifugation and washing steps. Selected aliquots of the reaction mixtures were also centrifuged through percoll to confirm that only RBC's (not white cells) bound the $^{125}$I-antigen. In some of these "whole blood" experiments, instead of using Alsever's as an anti-coagulant, blood was drawn into EDTA or citrate and used at once in a similar manner. A few comparable "whole blood" experiments were also performed with $^{125}$I-human IgG as the target antigen. In these experiments washed RBC's were dispersed in BSA-PBS, to avoid the potential confounding effect of endogenous serum-associated IgG. b) In other kinetic experiments one volume of RBC's was franked with saturating amounts of the heteropolymer, and after three washes was added to 10 volumes of anti-coagulated blood containing $^{125}$I-$DNP_{55}BGG$, and incubated at 37° C. Aliquots of the dispersions were processed periodically to determine RBC-associated $^{125}$I counts.

Direct binding of $^{125}$I-heteropolymers to a number of matrices was determined in procedures analogous to those described above. For example, duplicate aliquots of 100 ul of $^{125}$I-heteropolymer #4 (see below) were incubated for one hour at room temperature, with shaking, with either 100 ul of a 50% dispersion of human RBC's, or 100 ul of a 33% dispersion of human IgG-Sepharose. Samples were then subjected to two cycles of centrifugation and washing and the levels of matrix-bound $^{125}$I counts were determined. Direct binding to human RBC's of the $^{125}$I-heteropolymers was also determined as a function of time at 37° C.

Control experiments tested for the specificity of antigen binding by heteropolymer treated RBC's and verified the requirement for CR1. These experiments included the use of heteropolymer-treated sheep RBC's (which lack CR1), naive (untreated) human RBC's, and excess homologous monomeric Mabs (in ascites fluid) which blocked the action of the heteropolymers.

RESULTS

Preparation and Initial Characterizations of Heteropolymers

We prepared a number of heteropolymers by SPDP cross-linking, and examined the ability of these heteropolymers to react with human RBC's and facilitate binding of specific antigens. Preliminary data (Table 1), using mixtures of saturating amounts of unfractionated material (containing heteropolymers and non-cross-linked monomers), demonstrated specific RBC-associated binding of the $^{125}$I-antigens. An excess of $^{125}$I-antigen was used in order to determine the maximum number of ligands bound per RBC. For each heteropolymer mixture the results (Table 1) are in good agreement with the typical number of CR1 epitopes (200–500) recognized by the anti-CR1 Mabs.

Heteropolymer mixture #1 can facilitate binding via two noncompeting Mabs to CR1, 1B4 and HB8592. This mixture can, therefore, place approximately twice as many anti-IgG heteropolymers on the RBC's as a heteropolymer containing only one anti-CR1 Mab. The maximum $^{125}$I-human IgG bound to such "doubly-franked" RBC's is nearly equal to the sum of the $^{125}$I-IgG bound to RBC's franked with two individual components of the mixture (Table 1); this illustrates the principle of additivity. Dose-response experiments with heteropolymer #1 and other heteropolymers (Table 1, and see below) confirm that RBC binding of both heteropolymer and $^{125}$I-antigen is saturable. "Background" binding of antigen to naive RBC's is low, and use of heteropolymers with "irrelevant" specificities for the target ligands (e.g. 8E11 (anti-C3b) X HB8592) gave no binding (Table 1).

Binding Isotherms with Isolated Heteropolymers

Figure 1B:
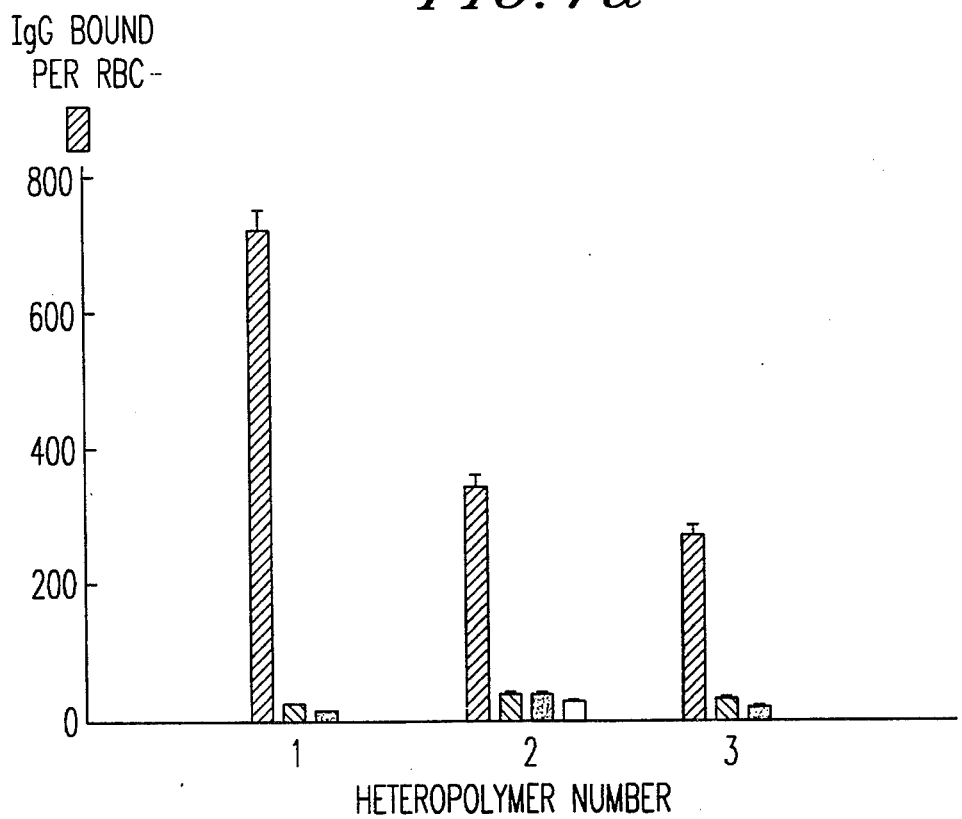
Figure 2:
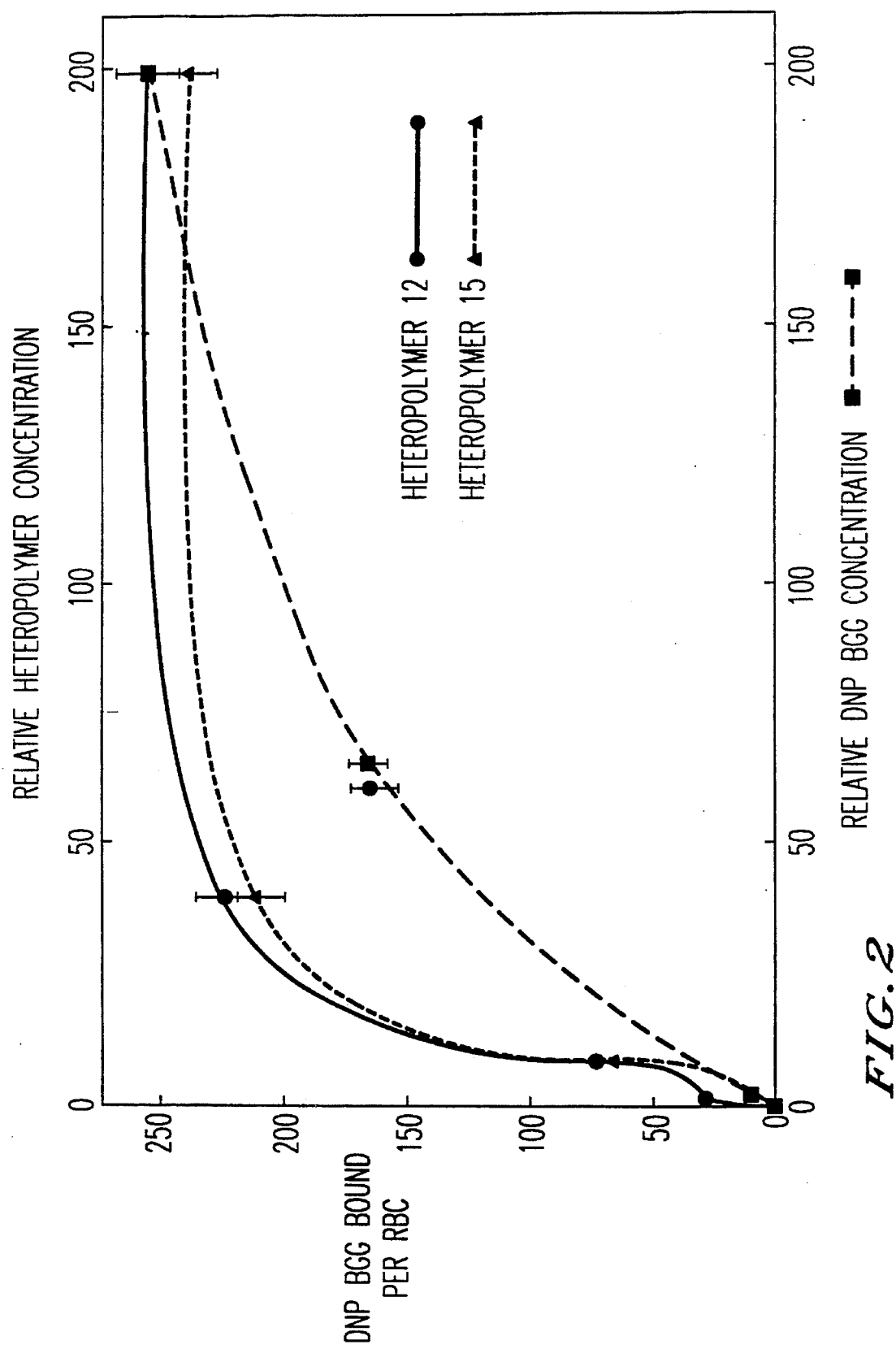
FIG. 2 is a graph of DNP BGG binding per red blood cell as a function of heteropolymer concentration. Heteropolymer 12 and heteropolymer 15 are tested.

Heteropolymer mixtures were further purified by gel permeation chromatography, and the highest mw subfractions (ca. corresponding to trimers and larger species) were used to quantitate binding (FIGS. 1a and 1b and 2). In these experiments binding of $^{125}$I-antigens to franked RBC's was determined, after two cycles of centrifugation and washing with BSA-PBS, by direct counting of the RBC pellets.

At saturating input of heteropolymer, the maximum number of antigen molecules bound per RBC is in good quantitative agreement with our initial survey results using unfractionated heteropolymer mixtures and centrifugation through oil to separate bound from free $^{125}$I-antigen. These experiments confirm that binding is saturable, since use of excess quantities of a single heteropolymer or $^{125}$I-antigen does not increase binding beyond the saturation level (typically 200–1000 antigens per RBC, FIGS. 1a and 1b and 2). Analysis of results with blood from two donors (FIGS. 1a and 1b) demonstrates that maximum binding reflects the number of CR1 epitopes per RBC characteristic of the individual donor. The principle of additivity is also illustrated in experiments in which RBC's were franked with a combined mixture of two heteropolymers (FIG. 1a). The combined action of the two heteropolymers in facilitating binding of the $^{125}$I-antigen is close to the sum of the action of each species individually.

Bi-specificity of the heteropolymers was demonstrated in inhibition experiments using an excess of homologous monomeric Mab. Our goal was either to block binding of heteropolymer to RBC's (using an appropriate anti-CR1 Mab to thus preclude binding of $^{125}$I-DNP$_{55}$BGG), or to inhibit directly binding of $^{125}$I-DNP$_{55}$BGG to franked RBC's (using the appropriate monomeric anti-DNP Mab). In all cases more than 90% of specific binding was reduced by these procedures (FIG. 1b). Sheep RBC's lack CR1, and as anticipated, heteropolymers directed against CR1 do not facilitate binding of the $^{125}$I-antigen to sheep RBC's (FIG. 1b). Finally, the dual specificities of two of the heteropolymer mixtures was confirmed by labelling them with $^{125}$I and examining their binding to human RBC's and to a Sepharose 4B matrix containing their respective target antigens (Table 2). The results demonstrate that the isolated polymers bind to both of their respective matrices, and also confirm that their direct binding to human RBC's is rapid at 37° C.

TABLE 1

Survey of Cross-Linked Mab Heteropolymer Mixtures in facilitating Antigen Binding to RBC's A. Binding of $^{125}$I-Human IgG

| Hetero Polymer # | Mab #1 (Specificity) × Mab #2 (Specificity)* | Molecules** IGG Bound/ RBC |
|---|---|---|
| 1 | 1B4(anti-CR1) × HB43 (anti-IgG) and HB8592 (anti-CR1) | 1150 |
| 2 | HB43(anti-IgG) × HB8592 (anti-CR1) | 601 |
| 3 | HB43(anti-IgG) × 1B4(anti-CRI) | 492 |
| 4 | HB43(anti-IgG) × HB8592(anti-CR1) | 357 |
| 5 | HB43(anti-IgG) × 1B4(anti-CR1) | 479 |
| 6 | HB43(anti-IgG) × 3D9(anti-CR1) | 355 |
| 7 | HB43(anti-IgG) × 57F(anti-CR1) | 387 |
| Control | 8Ell(anti-C3b) × HB8592(anti-CR1) | −2 |

B. Binding of $^{125}$I-(DNP)$_{55}$BGG

| Heteropolymer | Mab #1 (Specificity) × Mab #2 (Specificity)* | Molecules** DNP$_{55}$BGG Bound/ RBC |
|---|---|---|
| 8 | 3D9(anti-CR1) × 2A1(anti-DNP) | 191 |
| 9 | 3D9(anti-CR1) × 23D(anti-CR1) | 243 |
| 10 | 23D1(anti-DNP) × HB8592(anti-CR1) | 129 |
| 11 | 23D1(anti-DNP) × 1B4(anti-CR1) | 255 |
| 12 | 23D1(anti-DNP) × 3D9(anti-CR1) | 196 |
| 13 | HB8592(anti-CR) × 2A1(anti-DNP) | 95 |
| 14 | HB8592(anti-CR1) × 23D1(anti-DNP) | 133 |
| 15 | 1B4(anti-CR1) × 23D1(anti-DNP) | 279 |
| 16 | 1B4(anti-CR1) × 2A1(anti-DNP) | 236 |
| Control | 8E11(anti-C3b) × HB8592(anti-CR1) | −11 |

C. Demonstration of Saturation of Binding with Heteropolymer #1 and $^{125}$I-IgG

| Relative Heteropolymer Concentration | Relative $^{125}$I- Human IgG Concentration | Molecules** IgG Bound RBC |
|---|---|---|
| 5 | 5 | 994 |
| 5 | 1 | 868 |
| 5 | 0.2 | 343 |
| 1*** | 1**** | 777 |

TABLE 1-continued

Survey of Cross-Linked Mab Heteropolymer Mixtures in facilitating Antigen Binding to RBC's

| 0.2 | 1 | | 205 |
|---|---|---|---|

Table 1 footnotes
*For each heteropolymer listed, the first Mab was reduced with dithiothreitol (after reacting with SPDP) and then coupled to the second SPDP-reacted Mab. Heteropolymers #2 and #4 represent preparations with HB8592 purified via protein G and octanoic acid-50% saturated ammonium sulfate, respectively. Heteropolymer #1 was prepared by simultaneously reacting a cocktail of SPDP-coupled and reduced 1B4 and HB8592 with SPDP-coupled HB43.
**Binding was determined by centrifuging RBC's through oil. Background binding to naive human RBC's was 40 human IgG and 60 $DNP_{55}BGG$ per RBC respectively, and was subtracted to give the net specific binding reported. In parts A and B predetermined saturating inputs of both heteropolymer and $^{125}$I-antigen were used.
***"1" corresponds to 3.0 ug/ml of heteropolymer in a 12.5% hematocrit.
****"1" corresponds to 0.92 ug/ml $^{125}$I-human IgG in a 12.5% hematocrit.

TABLE 2

Binding of $^{125}$I-Labelled Heteropolymers to Human RBC's or to Sepharose Coupled Ligands

| | % Bound* | |
|---|---|---|
| | Human RBC's | IgG (or DNP)-Sepharose |
| #4, unfractionated mixture (HB43(anti-IgG) × HB8592(anti-CR1)) | 45 ± 5 | 55 ± 5 |
| #4, isolated polymer fraction | 65 ± 3 | 86 ± 5 |
| #11, unfractionated mixture (23D1(anti-DNP) × 1B4 (anti-CR1)) | 34 ± 6** | 86 ± 5 |
| #11, isolated polymer fraction | 72 ± 2*** | 85 ± 5 |

TABLE 2 footnotes
*Bound after incubation (with an excess of binding matrix) for one hour at either room temperature (Sepharose samples) and/or 37° C.(RBC's were examined at both temperatures). IgG Sepharose was used as the binding matrix for heteropolymer #4, and DNP-Sepharose (containing a dinitrophenylated Mab to IgM) was used for #11. All samples were corrected for background binding (5% or less) to sheep RBC's or naive (unreacted) Sepharose.
**Binding was 30% and 32% respectively after incubation for either two or five minutes at 37° C.
***Binding was 57% and 69%, respectively, after incubation for either two minutes or five minutes at 37° C.

METHODS OF USE

The franked RBC's described above have immediate application in a variety of research, clinical diagnostic, or therapeutic uses. The most important are therapeutic uses, which can include (1) using a franked RBC of the invention with specificity to an antigen such as HIV to clear free antigen from the blood of a human or primate patient, (2) using a franked erythrocyte with a Mab specific for a non-immunogenic but potentially "pathogenic" target such as LDL which has been linked to atherosclerosis and (3) using a franked erythrocyte with Mab specificity for the natural ligand of CR1 (such as C3b) where the number of naturally occurring receptors in an individual patient has decreased, such as in systemic lupus erythematosus. Of course, the specific antigens or antibody targets identified above are exemplary only, and virtually any circulating microorganism, virus, compound and the like to which a Mab can be prepared can be subject to therapeutic treatment through the invention.

The franked erythrocytes may be prepared and introduced for therapeutic use in either of three methods. First, the bi-specific heteropolymer comprised of at least two cross-linked Mab, one specific for the RBC and the other for the antigen, may be introduced directly to the bloodstream through inoculation. Alternatively, a small amount of RBC's can be extracted from the patient, and bound to the heteropolymer in sterile in vitro conditions and then reintroduced into the patient. Finally, in cases of low CR1 or low RBC disease states, franked erythrocytes from a compatable heterologous matched blood donor can be used. In any of the above examples, a "cocktail" of several heteropolymers (see results section) can be used. Given the high binding capacity of the heteropolymer to the RBC, direct injection of the heteropolymer can be as effective as in vitro preparation of the franked erythrocyte, followed by inoculation.

In addition to taking advantage of the body's natural defenses by augmenting the natural immune defense system, binding the heteropolymer to the RBC's (either in vitro or in vivo) may reduce or remove any "immunogenicity" that would be characteristic of Mabs prepared from mouse hosts and the like. In fact, currently, the vast majority of monoclonal antibodies are produced in mice. Mab treatment thus suffers, at least to some degree, from the body's natural immune response against the mouse Mab which would thus prevent the Mab from binding to its target antigen. As the number of heteropolymers bound per RBC is relatively small (below about 500) the Mab itself may not be recognized as foreign, and the host immune response may not be triggered, or at least, will be significantly reduced. Use of available human Mabs to prepare heteropolymers should also eliminate any host immune response.

The dosage and treatment regimen will vary from antigen to antigen, individual to individual, and disease state. In general, these can be determined on an empirical basis. An extreme minority of available RBC's may be used effectively in conferring therapeutic treatment. This is due in part to the vast numbers of RBC's present in the blood, in contrast to most antigens. As an example, the level of HIV which circulates free in the blood has been suggested as the most cytopathic form of HIV. High levels of HIV in the circulation appear to correlate with disease activity. Yet, this level ranges between 1,000 and 50,000 virus particles per ml. Ho et al, *New England Journal of Medicine,* 321, 1621–1625 (1989), Coombs et al., *ibid,* 1626–1631. In contrast, the number of RBC per ml in circulation is many orders of magnitude greater, and accordingly, even a small minority of available RBC's treated according to the claimed invention should be sufficient to confer therapeutic treatment, given the appropriate anti-CR1/anti-HIV franked RBC. As exemplary levels only, in the treatment of AIDS, an intravenous administration of no more than 1–4 mg of appropriate heteropolymer should be sufficient to frank the patients' RBC's for quantitative binding of circulating HIV. With sufficiently high avidity anti-HIV antibodies in the heteropolymer (easily achieved by standard methods) it should be possible to use considerably less heteropolymer (μg amounts). See the "Detailed Caclulations Section" for a more complete analysis of this problem. Alternatively, if the RBC's of the patient are first removed and franked with heteropolymer and then re-injected, the dose administration of franked erythrocytes would be considerably less than 1 "unit" (1 pint) of blood. Use of ca. 50–100 ml of franked RBC's (a few % of total circulating RBC's) should be adequate). The low levels needed are a consequence of the fact that even under conditions of high disease activity the concentration of infectious agent in the blood (e.g. HIV) is many orders of magnitude lower than the concentration of RBC's.

This invention has been described by reference both to generic description and specific embodiment. Examples provided are not intended to be limiting unless so specified, and variations will occur to those of ordinary skill in the art without the exercise of inventive faculty. The invention embraces these alternatives, save for the limitations imposed by the claims set forth below.

What is claimed is:

1. A method of therapeutically treating a primate individual with a target antigen present in its circulatory system, said target antigen being selected from the group consisting of a virus, a microorganism and a protein, comprising administering to said individual a therapeutically effective amount of a monoclonal antibody heteropolymer comprising a first monoclonal antibody specific for CR1 receptor cites on the surface of erythrocytes of said individual, said first monoclonal antibody being cross-linked to a second monoclonal antibody specific for said target antigen.

2. The method of claim 1, wherein said monoclonal antibodies are obtained from a non-human host.

3. The method of claim 1, wherein said antibodies are obtained from a human host.

4. The method of claim 1, wherein said antigen is a virus.

5. The method of claim 1, wherein said antigen is a microorganism.

6. The method of claim 1, wherein said antigen is a protein.

* * * * *

UNITED STATES PATENT AND TRADEMARK OFFICE
CERTIFICATE OF CORRECTION

PATENT NO. : 5,487,890
DATED : January 30, 1996
INVENTOR(S) : Taylor, Ronald P., Sutherland, William M., Reist, Craig It is certified that error appears in the above-indentified patent and that said Letters Patent is hereby corrected as shown below:

At Column 1, Line 12, the following paragraph is inserted:

-- U.S. Government Rights

This invention was made with United States Government support under Grant No. AR 24083 awarded by National Institutes of Health. The United States Government has certain rights in the invention. --

Signed and Sealed this

Seventeenth Day of April, 2001

Attest:

NICHOLAS P. GODICI

Attesting Officer

Acting Director of the United States Patent and Trademark Office